United States Patent
Hirsh

(10) Patent No.: US 7,645,238 B2
(45) Date of Patent: Jan. 12, 2010

(54) REGIONAL ANESTHETIC METHOD AND APPARATUS

(75) Inventor: Robert Hirsh, Merion Station, PA (US)

(73) Assignee: The Cooper Health System, Camden, NJ (US)

( * ) Notice: Subject to any disclaimer, the term of this patent is extended or adjusted under 35 U.S.C. 154(b) by 411 days.

(21) Appl. No.: 11/292,681

(22) Filed: Dec. 2, 2005

(65) Prior Publication Data

US 2007/0167829 A1    Jul. 19, 2007

(51) Int. Cl.
*A61B 8/14* (2006.01)

(52) U.S. Cl. .............. 600/464; 600/437; 600/449; 600/461; 600/463; 600/467; 604/264

(58) Field of Classification Search ......... 600/437–466, 600/471; 604/264
See application file for complete search history.

(56) References Cited

U.S. PATENT DOCUMENTS

| | | | |
|---|---|---|---|
| 4,808,157 A | | 2/1989 | Coombs |
| 4,887,606 A | * | 12/1989 | Yock et al. ................. 600/461 |
| 5,156,596 A | * | 10/1992 | Balbierz et al. ........ 604/164.11 |
| 5,259,385 A | * | 11/1993 | Miller et al. ................ 600/453 |
| 5,480,421 A | | 1/1996 | Otten |
| 5,484,416 A | * | 1/1996 | Gittings ................. 604/164.08 |
| 5,685,852 A | * | 11/1997 | Turkel et al. ................. 604/159 |
| 5,779,642 A | * | 7/1998 | Nightengale ................. 600/461 |
| 5,779,643 A | * | 7/1998 | Lum et al. ................... 600/462 |
| 5,902,245 A | * | 5/1999 | Yock .......................... 600/463 |
| 5,972,012 A | | 10/1999 | Ream et al. |
| 6,679,899 B2 | | 1/2004 | Wiener et al. |
| 6,795,737 B2 | | 9/2004 | Gielen et al. |
| 6,981,947 B2 | | 1/2006 | Melker |
| 7,328,064 B2 | * | 2/2008 | Mathiesen et al. ............ 604/21 |
| 7,555,343 B2 | * | 6/2009 | Bleich .......................... 607/43 |
| 2001/0051766 A1 | | 12/2001 | Gazdzinski |
| 2003/0236489 A1 | | 12/2003 | Jacobson et al. |
| 2005/0033551 A1 | | 2/2005 | Takai et al. |

* cited by examiner

*Primary Examiner*—Long V Le
*Assistant Examiner*—Sanjay Cattungal
(74) *Attorney, Agent, or Firm*—Cozen O'Connor; Michael B. Fein

(57) ABSTRACT

A system and method for regional anesthesia using ultrasound to assist in locating the anesthetic needle are disclosed. One or more piezo-electric crystal transducers is placed either at the tip of the needle or near the tip of the needle on a stylet which is inserted into the lumen of the needle. The transducer(s) are pulsed with ultrasonic frequency, the reflected ultrasonic signals from structures are detected and converted into a digital signal and may be displayed in an oscilloscopic format to indicate anatomical structures forward to the needle and allow the medical professional to avoid errors and/or increase efficiency and accuracy. An array of transducers can be pulsed in a phased array fashion to generate a 2D image, or a single transducer can be pulsed to generate a 1D image.

7 Claims, 2 Drawing Sheets

REGIONAL ANESTHETIC METHOD AND APPARATUS

FIELD OF THE INVENTION

This invention relates generally to the field of regional anesthesia, epidural needles and methods of placement of epidural needles and other regional anesthesia needles.

BACKGROUND OF THE INVENTION

Regional anesthesia involves the introduction of local anesthetics, with the intention of blocking the nerve supply to a specific part of the body so the patient cannot feel pain in that area when a surgical operation is performed, for pain relief during onset of labor or during labor, or for chronic pain. Regional anesthesia is used in both epidural and subdural or spinal procedures, and can involve plexus blocks and blocks of peripheral nerves.

Epidural anesthesia, one form of regional anesthesia, has gained popularity over the years as being an effective manner of blocking pain without requiring entry to the dura mater of the spinal cord (i.e., a spinal anesthesia). In fact, epidural anesthesia is often the anesthesia of choice in child birth. The surgical procedure for epidural anesthesia typically starts with the utilization of a 17- or 18-gauge Touhy needle in the lumbar region in order to puncture the skin, and to traverse at least the supraspinous ligament. The Touhy needle is basically a hollow needle having an angled distal tip which is slightly curved (i.e., a Huber point) and a proximal luer fitting, and a solid stylet which sits inside and substantially fills the hollow needle. Once the skin and supraspinous ligament have been traversed by the Touhy needle, the solid stylet is removed from within the hollow needle, and an air filled syringe is coupled to the proximal luer fitting of the hollow needle. With pressure being applied to the plunger of the syringe as well as to the barrel of the syringe, the hollow needle of the Touhy needle is slowly advanced past the interspinous ligament and ligamentum flavum until the needle enters the epidural space between the ligamentum flavum and the dura mater of the spine. Location of the epidural space which is filled with connective tissue, fatty tissue, and blood vessels is indicated by loss of resistance; i.e., less resistance to the injection of air through the needle. In other words, when the pressure applied by the practitioner to the plunger causes the plunger to readily push air through the needle, the practitioner can assume that the epidural space has been reached. Upon entry to the epidural space, the syringe is carefully disconnected from the hollow needle (extreme care being taken to keep the needle in its exact position), and a catheter is threaded through the hollow needle. Because the hollow needle has an angled distal end, upon reaching the distal end of the hollow needle, the catheter is directed into the epidural space which is substantially perpendicular to the direction of the needle. The catheter is advanced only two to three centimeters into the epidural space in order to reduce the likelihood that it might exit though an intervertebral foramen, with resulting inadequate epidural anesthesia. With the catheter in place, a test dose, repeated injections, or a continuous flow of anesthesia may be administered through the catheter.

A conventional method of placing regional anesthetic needles is to use anatomical landmarks, tapping on the barrel of an attached syringe to feel the way forward until a loss of resistance is obtained. Because the person placing the needle must rely on tactile information, the incidence of errors such as dural punctures, wet taps during lumbar epidurals, and spinal chord injury during cervical or thoracic epidural placements is a serious problem.

While the apparatus and methods for administering regional anesthesia have proved successful over a long period of time, there are drawbacks to those approaches and methods. With regard to the Touhy needle in particular, although it is provided with a curved Huber point, the Touhy needle is still sharp. Use of the Touhy needle therefore runs the risk that the practitioner, i.e., physician, operator, or other person trained to perform this procedure, might overshoot the epidural space and enter the subdural space between the dura mater and the arachnoid mater of the spine, or the subarachnoid space. Such a mistake could result in extreme over-application of anesthesia with a possible high level of spinal anesthesia, necessitating endotracheal intubation of the trachea and mechanical ventilation of the patient. Similar complications could also occur during the disconnection of the syringe from the Touhy needle and insertion of the catheter, as the patient might move, or the needle might not be held properly in position. Such movement of the needle could result in the undesirable entry of the needle and/or catheter into the subdural or subarachnoid spaces.

In order to obtain better information during regional anesthesia needle placement, it has been proposed to use X-ray fluoroscopic techniques to place the needles, but in many cases it is not possible to use X-ray, for example in the case of pregnant women or at the bedside in the trauma intensive care unit (TICU).

Recently it has been proposed to use 2-D echo to facilitate placement of regional anesthetic needles. MicroMaxx™ hand-held ultrasonic devices, manufactured by SonoSite, Inc., which use 2D ultrasound on the patient's skin, have been used at Dartmouth-Hitchcock Medical Center to assist in proper placement of the needle. The use of a 2D echo device is complicated by the need for the use of an acoustic gel, which can compromise sterility when used to assist with regional anesthetic needle placement. Moreover, the 2D echo device is not useful for imaging structures inside the bony spinal canal because the structure of bone tissue scatters ultrasound randomly, such that no intelligible image can be obtained from sound reflected from tissue structures that are deep to bone.

Accordingly there exists a long-felt and continuing need for apparatus and methods for placement of epidural needles and other regional anesthesia needles.

SUMMARY OF THE INVENTION

It is therefore an object of this invention to provide apparatus and methods for safer and easier regional anesthesia. It is another object of the invention to provide apparatus for use in a guided method of placing needles for regional anesthesia which do not suffer from the disadvantages of currently used techniques and apparatus.

It is also an object to provide an improved epidural needle system and an improved method for epidural injections which provides better anatomical information than mere tactile information.

These objects and others which will become apparent from the following disclosure and drawings are achieved by the present invention which in some aspects comprise a system for regional anesthesia comprising (A) a needle having a lumen, a length, and a tip, (B) an optional stylet having a length and a tip, the stylet adapted to be inserted into the lumen of the needle, (C) a piezo-electric transducer means, (D) means for pulsing the transducer with ultrasonic frequency, (E) means for detecting reflected ultrasonic signals from structures; and (F) means to convert the reflected ultrasonic signals into a digital signal; and (G) means to display the digital signal; the transducer means located either at the tip of the needle or at the tip of the optional stylet.

In some aspects the invention comprises a method of placing a regional anesthetic needle comprising providing a piezo-electric crystal located at or near the tip of the needle, pulsing the transducer with ultrasonic frequency, detecting reflected ultrasonic signals from structures deep to the tip of the needle; converting the reflected ultrasonic signals into a digital signal representing anatomical information forward to the needle; displaying the digital signal, and guiding the needle to a desired location while preventing the needle from touching an undesired location. "Deep to the tip" and "forward to the needle" are used interchangeably to refer to the anatomy of the patient distal to the tip of the needle as it is being placed. "Desired location" refers to the placement of the needle in a safe and proper anatomical area.

Suitable regional needles have a distal end and a proximal end, with the distal end terminating in an aperture and having a tip adapted for insertion through tissue into a nerve sheath of a patient, and with the proximal end being adapted for fluid connection. In the case of Touhy needles which are typically used for epidural anesthetics, the tip on the distal end has a beveled aperture.

In some embodiments the system comprises a stylet. Stylets are conventionally used when regional anesthetic needles are placed, and any of the conventional stylets can be used with the system of the invention, or a special stylet with one or more piezo-electric transducer(s) on the tip can be used. Such stylets are disclosed in Gittings, U.S. Pat. No. 5,484,416, and in Yock, et al., U.S. Pat. No. 4,887,606, each of which is incorporated by reference in its entirety. Electrical wires can be provided through the stylet to connect the transducer(s) to the opposite end of the stylet when they are present at the tip of a stylet used in the present invention, as shown in Yock, et al., so that the ultrasound signal can be sent to and received from the transducer(s).

Suitable transducers include but are not limited to small piezo-electric crystals which are commercially available, for example a 20 MHz PZTSA transducer having a 1 mm diameter. In some embodiments, a single transducer is used. In some embodiments, an array of transducers comprising at least two transducers, is used. The transducer or transducers can be bonded to the stylet or tip of the needle itself with any means, including, for example, an adhesive such as Emerson IG0101 microballoons in epoxy. Electrical conductive material can be used in addition to the wires, or instead of one conductor, for example Trabond 2902 silver epoxy is suitable for this purpose. In some embodiments the transducer or transducers are encapsulated in a sleeve, for example a polyimide or other plastic sleeve. Suitable wiring systems are used to connect such arrays to the ultrasound signal generation and reception system, and suitable electronics and software may be used to convert the signal to a displayed graph which can be interpreted by the medical professional and used to guide the placement of the needle.

When one transducer is used, a 1D graphical representation of amplitude with respect to time can be displayed for the benefit of the operator. "Operator" as used herein refers to a physician, other trained professional, student or other trainee. By looking at the signal from the acoustic interface between dura matter and cerebrospinal fluid (CSF), the operator can judge distance between the needle tip and dura, and thereby avoid puncturing the dura.

When two or more transducers are used in an array, a 2D image of tissues distal to the needle can be displayed by activating the transducers in a phased array fashion to sweep the beam radially from the point of the needle with appropriate controller and software. Because the needle is close to the structure, and since attenuation increases with frequency and distance, in some embodiments it is possible to use much higher frequencies than conventionally used. Although 1D images are useful to assist with placing needles used for regional anesthetics, 2D images distal to the needle allow the operator to see cross sections of the spinal cord, nerve roots, and cauda equina, for example.

Means for pulsing suitable for use in the present invention include conventional signal generators and power supplies capable of generating an ultrasound signal at the transducer. Conventional electronics may be used to receive the reflected ultrasound signals and convert analog to digital signals. Conventional programmed microprocessors may be used to convert the reflected ultrasound signals to, for example, a simulation of an oscilloscope displayed on a computer display, for example on a laptop computer or other computer suitable for an operating room environment.

The regional anesthetic needle system of the invention uses the transducer means at the tip of the needle or the stylet to obtain an ultrasound image of the anatomy of the patient distal to the needle, to gauge depth, and thereby assist with the accurate and safe placement of the regional anesthetic needle.

In addition to the ultrasound imagery, the system in some embodiments includes means, such as controller programming and a signal module, to generate an audible signal indicating the distance between the tip of the needle and the tissues distal to the tip. In such embodiments, the operator can use the audible signal to assist in placing the needle. In some embodiments the system can increase the number of sounds or pitch as the tip gets closer to tissue structure.

BRIEF DESCRIPTION OF THE DRAWINGS

An embodiment of the invention is illustrated in the drawings and will be described in more detail below with reference thereto. The illustrated embodiment is only one example of the invention and the description thereof is not intended to imply a limitation on the invention. The invention is capable of considerable modification, alteration and equivalents in form and function.

DESCRIPTION OF THE INVENTION

Figure 1:
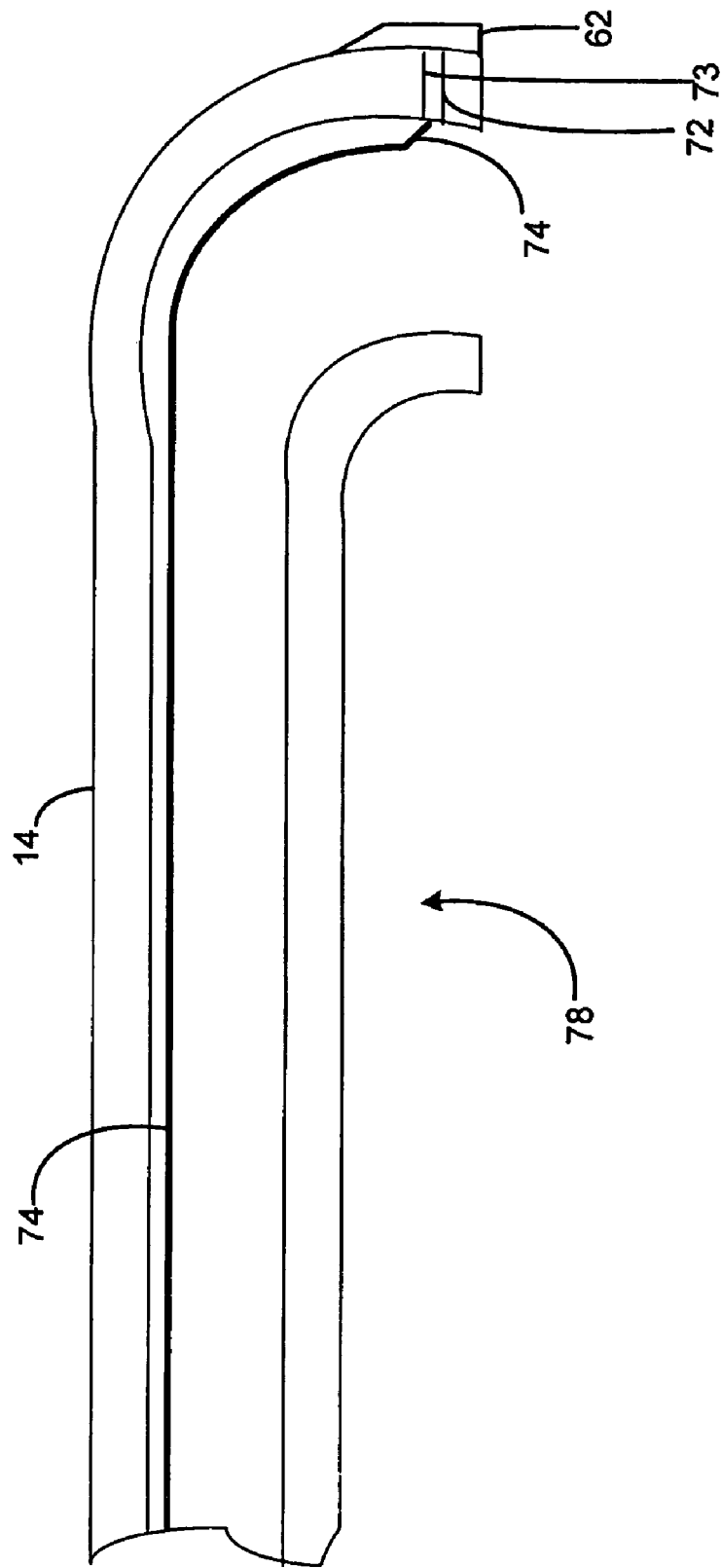
FIG. 1 is a partial cross-sectional view of a Touhy needle having a transducer at the distal end.

FIG. 1 shows an embodiment of a regional anesthetic needle 78 according to the invention wherein a conventional Touhy needle 14 is modified by providing a piezo-electric crystal 62 on the distal portion of the needle, connected by wires 72, 73 through the front of the needle, and the wire 74 continuing through the lumen of the needle. The wire 74 can be adhered to the inside wall forming the lumen. In some embodiments conductive material is used rather than wire, for example conductive polymers can be adhered to the inside wall of the lumen.

Figure 2:
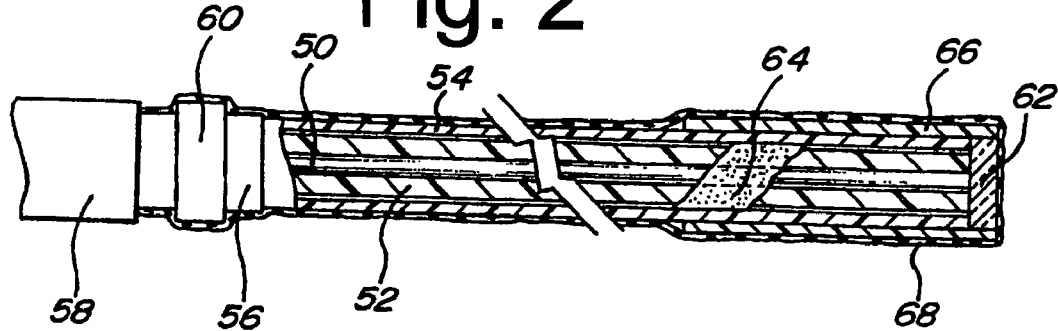
FIG. 2 is a partial cross-sectional view of a stylet having a transducer at the distal end.

FIG. 2 shows an embodiment of stylet 16 having a transducer 62 at the distal end. A solid center conductor 50 is surrounded by a dielectric tube 52. The conductor in this embodiment is surrounded by a Teflon dielectric tube, which provides improved noise suppression during operation. Conductor 50 can be composed of copper, silver, or silver-plated copper. A conductive adhesive 54 is coextruded over dielectric tube 52 which is a thin layer of nylon, capable of being adhered to by conductive adhesive. Shielding means 56 covers a portion of dielectric tube 52. Shielding means 56 is a braid or a foil wrap over a drain wire. A silicon, Teflon or other type of jacket 58 completes a portion of the probe-cable assembly. Jacket 58 and shielding means 56 are preferably stripped off the dielectric tube 52, leaving about ¼ of an inch of the shielding means exposed. Anchoring means 60 anchors shielding means 56 to dielectric tube 52. Anchoring means 60 can be a conductive ring or hollow cylindrical crimp. The exposed length of dielectric tube 52 extending beyond shielding means 56 can be any preselected length necessary, depending on the maximum length of needle with which the probe is intended for use.

Figure 3:
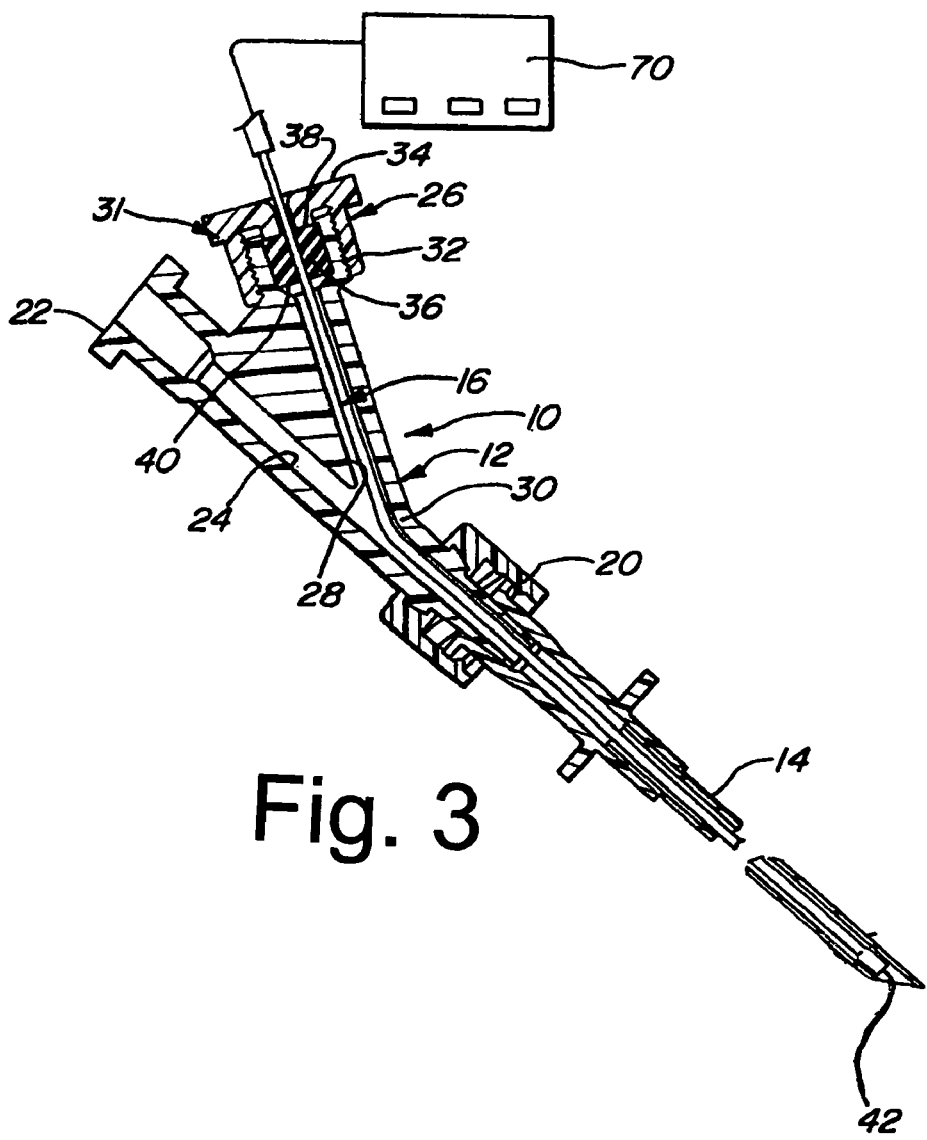
FIG. 3 is a partial cross-sectional view of a regional anesthetic needle and stylet assembly.

FIG. 3 illustrates needle assembly 10 including housing 12, needle 14 and stylet 16. Housing 12 includes first end 20 adapted to be connected to a variety of needles. Second end 22 is axially opposite first end 20 and preferably coaxial with first end 20. Second end 22 is adapted to be connected to a syringe, for example. Housing 12 includes first channel 24 defined between first end 20 and second end 22. Third end 26 is adapted to receive stylet 16. A second channel 28 is defined between third end 26 and a medial location along first channel 24 that defines a bend 30. As illustrated, when in use, stylet 16 is axially movable through second channel 28 and a portion of first channel 24 and needle 14 such that stylet 16 bends around bend 30. First channel 24 and second channel 28 typically have a relative angle of orientation of approximately 30 degrees.

Third end 26 preferably includes locking means 31. Locking means 31 includes external threads 32 which can be formed on third end 26 of housing 12. Internally threaded adjustable member 34 is received over external threads 32. Pressure means 36 is contacted by surface 38 on adjustable member 34. Pressure means 36 is received in the portion of housing 12 indicated at 40 such that the relative adjustment of member 34 along external threads 32 causes surface 38 to bear against and apply an axial pressure on pressure means 36. Such axial pressure compresses pressure means 36 in such manner that pressure means 36 exerts a radially compressive force on stylet 16. In this manner, stylet 16 is temporarily held axially fixed relative to housing 12. Pressure means 36 also acts as a seal against leakage from the third end 26.

A novel system and method for regional anesthesia using ultrasound to assist in locating the anesthetic needle has been described. One or more piezo-electric crystals are placed either at the tip of the needle or near the tip of the needle on a stylet which is inserted into the lumen of the needle. The ultrasound signal from the transducer is keyed or pulsed with ultrasonic frequency, the reflected ultrasonic signals from structures are detected and converted into a digital signal and displayed for the operator to indicate anatomical structures forward, i.e., distal, to the needle and allow the operator to avoid errors. The display may be in an oscilloscopic format.

While the invention has been described and illustrated in sufficient detail that those skilled in this art can readily make and use it, various alternatives, modifications, and improvements should become readily apparent without departing from the spirit and scope of the invention. All cited references are hereby incorporated by reference.

What is claimed is:

1. A method of placing a regional anesthetic needle comprising providing piezo-electric transducer located at or near the tip of the needle, keying an ultrasound signal from the transducer, detecting reflected ultrasound signals from dura matter structures distal to the tip of the needle; converting the reflected ultrasound signals into a digital signal representing distance between the tip of the needle and dura matter forward to the needle; displaying the digital signal; and guiding the needle to a desired location by using the displayed digital signal, thereby preventing the needle from touching the dura matter.

2. The method of claim 1 wherein the needle is a Touhy needle and contact with the dura is prevented by gauging the depth of the needle relative to the dura using the graphical display of ultrasound signals.

3. The method of claim 1 wherein the piezo-electric transducer is located on a stylet which is placed in the needle.

4. The method of claim 1 wherein an away of transducers at or near the tip of the needle are provided, keying the transducers in a phased array fashion to sweep a beam radially from the tip of the needle so as to generate a two dimensional (2D) image of tissues distal to the tip.

5. The method of claim 1 wherein means to generate an audible signal indicating the distance between the tip of the needle and the tissues distal to the tip is provided, and wherein the operator uses the audible signal to assist in placing the needle.

6. The method of claim 1 further including mechanically sweeping the transducer and generating a 2D image of the anatomy distal to the needle.

7. The method of claim 1 further including controlling the direction of the transducer by providing an electronically controlled lens or shutter distal to the transducer to reciprocate the direction.

* * * * *